United States Patent [19]
Weinheimer et al.

[11] 3,976,679
[45] Aug. 24, 1976

[54] NOVEL COMPOUNDS FROM CORAL

[76] Inventors: Alfred J. Weinheimer, 1206 Oklahoma, Norman, Okla. 73069; Robert L. Spraggins, 4151 Byron, Palo Alto, Calif. 94306

[22] Filed: July 23, 1970

[21] Appl. No.: 57,785

[52] U.S. Cl............... 260/408 D; 260/514 D; 260/488 R; 424/305; 424/317
[51] Int. Cl.$^2$..................... C07C 177/100
[58] Field of Search............ 260/468 D, 514 D, 488

[56] References Cited
UNITED STATES PATENTS

| | | | |
|---|---|---|---|
| 3,759,978 | 9/1973 | Lincoln et al...................... | 260/468 |
| 3,899,526 | 8/1975 | Schneider........................... | 260/468 |
| 3,900,513 | 8/1975 | Hamilton et al.................... | 260/468 |

OTHER PUBLICATIONS
Schneider et al., J.A.C.S., 94 2122, (1972).
Bundy et al., J.A.C.S., 94 2124, (1972).
Ranwell et al. Nature 221,1251 (1969).

*Primary Examiner*—Robert Gersil
*Attorney, Agent, or Firm*—Arnold, White & Durkee

[57] ABSTRACT

Novel compounds of the formula

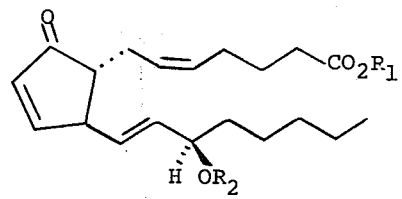

wherein $R_1$ is hydrogen or methyl, $R_2$ is hydrogen or acetyl and the diester thereof. The compounds are useful as intermediates for preparing biologically active prostaglandins and they are useful singly as antibacterial agents.

19 Claims, No Drawings

NOVEL COMPOUNDS FROM CORAL

BACKGROUND OF THE INVENTION

This invention concerns new and useful compounds related to prostaglandins and to the processes for the isolation of these compounds. The new compounds of the invention have the structure as follows:

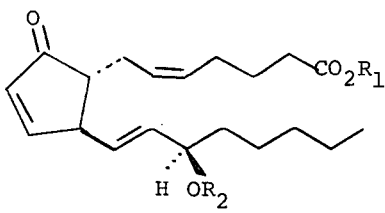

wherein $R_1$ is H, or $CH_3$ and $R_2$ is H or $CH_3CO_2-$. These compounds may be further characterized in that they may be obtained in a substantially pure form. The novel compounds of this invention as illustrated by the generic formula are isolated from the gorgonian, *plexaura homomalla* (Esper). The *Plexaura homomalla* consists of an outer cortex and an inner skeleton. The novel compounds of the invention can be isolated from the intact gorgonian or from the outer cortex that can be separated from the inner skeleton. The cortex can be easily separated from the skeleton in either a wet or dry form. When the dry form is employed, the gorgonian is air dried for several days at room temperature and the cortex stripped from the skeleton. Next, the cortex is ground to a fine mesh size in a conventional laboratory grinder. The resulting ground material is then extracted with an organic solvent or with an aqueous media that forms an aqueous emulsion that itself can be extracted with an organic solvent to produce a crude extract of the gorgonian, *Plexaura homomalla*.

Next, the crude extract is separated by chromatographic procedures, such as column, paper or the like, to obtain the novel compounds, which are identified by conventional laboratory techniques.

DETAILED DESCRIPTION OF VARIOUS EMBODIMENTS

The following examples are given simply to illustrate this invention, but they are not in any way to limit its scope.

EXAMPLE 1

Preparation of 15(R)-hydroxy-9-oxo-5-cis, 10,13-transprostatrienoic acid (15-epi-PGA$_2$). First, 450 grams of gorgonian *Plexaura homomalla* is freshly dried at room temperature and the cortex stripped from the inner skeleton. Then the removed cortex is ground to a fine mesh, and the ground cortex is extracted with commercially available hexane. The cortex is extracted by placing the ground cortex in a conical filter funnel equipped with filter paper and extracted with hexane by passing the hexane over the ground cortex until the resulting solution showed no color. The excess solvent from the extraction is removed on a conventional rotary evaporator, and the last traces of solvent are removed using a high vacuum pump system until a constant weight is observed. About 43 grams of hexane extractables are extracted from the employed quantity of gorgonian.

Next, the hexane extract is subjected to conventional fractionation techniques. The fractionation technique employed in this run consists of first column chromatography of a 2.5 inch diameter column packed with 490 grams of silicic acid (sold as silicar CC-7) using benzene as the solvent for the packing procedure. Next, 83 grams of the crude extract obtained according to the procedure described immediately above, is placed on the column in a benzene solution and it is washed into the column with benzene. The crude extract is then eluded from the column using measured volumes of solvents of increasing polarity as follows: first, 4000 ml of benzene; second, 1000 ml of 20% ethylacetate in benzene; third, 1000 ml of 40% ethylacetate in benzene; fourth, 1000 ml of 60% ethylacetate in benzene and fifth, 1000 ml of ethylacetate. The percent recovered is 90.6.

Further purification is performed by packing 70 grams of silicic acid (CC-4) into a 1.25 inch diameter column as a benzene slurry. After packing the column it is washed with about 500 ml of benzene. A 0.740 gram sample obtained from the 60% ethylacetate benzene 2.5 inch column fraction is introduced into the column with benzene and chromatographed using 20% ethylacetate in benzene as the solvent. The flow rate for the column is 3 ml per minute and 100 ml fractions are taken, for a total of 17 fractions. The novel compound was identified as being in fractions 10 through 17 by thin layer chromatography using 1:99 acetic acid: ethylacetate as the solvent and silica gel H. plates.

The isolated compound exhibited the following instrumental analytical results: the mass spectrum is consistent with the structure with peaks at m/e 334, 316, 245 and 190; ORD spectrum $\alpha_{254}$=7.216°(peak), $\alpha_{212}$= −6,455°(trough); uv max (CH$_3$OH) 217 M$\mu$; NMR spectrum shows peaks at δ7.50 (1, dd, J=2,6Hz), 6.18 (1, dd, J=2,6Hz), 5.16 (z,m), 5.43 (z,m), 4.10 (1,m), 3.24 (1,m) and 0.90 (3, perturbed triplet). The IR spectra shows peaks at 1705, 1585, 1480, 1455, 1435, 1405, 1375, 1345, 1305, 1220, 1175, 1145, 1140, 1045, 1005, 960, 835, 745cm$^{-1}$ and IR (CDCl$_3$) 1710, 1590, 1480, 1440, 1410, 1380, 1350, 1235, 1215, 1175, 1080, 1045, 1010 and 970cm$^{-1}$.

EXAMPLE 2

Preparation of methyl 15-(R)-acetoxy-9-oxo-5,cis,10,13-trans-prostatrienoate (methyl, acetatediester of 15-epi-PGA$_2$). Following the procedure of Example 1, a sample obtained from the 2.5 inch column is further purified as follows: first, 70 grams of silicic acid (CC-4) is packed into a 1.25 inch diameter column as a benzene slurry. After preparing the column, it is washed with about 500 ml of benzene. Next, 1.5 grams of the sample obtained from the 20% ethylacetate in benzene fraction of the 2.5 inch column is washed into the smaller 1.25 inch column, with benzene. The fraction is eluted from the latter column by using 8% ethylacetate in benzene, and at a flow rate of 2 ml per minute, and 13 50 ml fractions were taken. Fractions 6 to 12 contain the prostaglandin diester. Thin layer chromatography is used to identify the novel diester. The analytical results are as follows: high resolution mass spectrum (m-60=330.2187; i.e., C$_{21}$H$_{30}$O$_3$): The mass spectrum showed peaks at m/e of 390, 359, 330 and 190 (base peak); ORD spectrum (CH$_3$OH) $\alpha_{217}$=6740° peak, $\alpha_{218}$= −5154° (trough) uv max (MeOH) 215 m$\mu$, $\epsilon$= 9,300. The IR spectra shows peaks at IR (film) 1735, 1710, 1585, 1455, 1435, 1370, 1310, 1240, 1165, 1015, 965, 885, 810, and 720 cm$^{-1}$ and IR (CHCl$_3$) 1730, 1710, 1585, 1455, 1435, 1370, 1310, 1240, 1205, 1170, 1145, 1015, 965 and 880 cm$^{-1}$. The NMR spectrum (CCl$_4$) shows peaks δ7.44 (1,dd, J=z,6Hz), 6.12 (1,dd, J=2,6 Hz), 5.48 (4 proton vinyl envelop), 5.14 (1,m), 3.61 (3,6) 1.98 (3,S), and 0.89 (3, perturbed triplet).

EXAMPLE 3

Preparation of methyl 15(R)-hydroxy-9-oxo-5-cis,10,13-trans-prostatrienoate. A 100 mg sample of methyl 15(R)-acetoxy-9-oxo-5-cis,10,13-trans-prostatrienoate is dissolved in about 15 ml of methanol blanketed under dry nitrogen. About 1 drop of concentrated HCl is added and the solution is stirred for about 16 hours at room temperature. At the end of the stirring time, the reaction medium is transferred to a separatory funnel with 50 ml of chloroform. Next, 50 ml of distilled water is added and the mixture shaken to cause partitioning of the reaction products between the immiscible layers. The aqueous layer is separated and then it is extracted with 2 additional portions of chloroform. The combined organic layers are dried over anhydrous sodium sulfate, and on evaporation of the solvent a yellow oil is produced. After chromatography on silicic acid approximately 50% yield of the methyl ester is obtained. The compound by NMR shows a singlet methyl signal for the —OMe, one exchangeable proton and a complete absence of the acetate signal in the starting compound. Thin layer chromotography of this material on silicia gel H plates using 40:60 ethylacetate in benzene as solvent showed a single spot with an R$_f$ value identical to an unpurified component of the crude extract of the gorgonian.

EXAMPLE 4

In this example, the *Plexaura homomalla* extractions were done on freshly dried specimens that were air dried for two and one-half months at about 90°F. The dried sample was solvent extracted as in Example 1 to obtain the desired product.

EXAMPLE 5

A freshly collected wet sample of gorgonian *Plexaura homomalla* is extracted with benzene in a normal fashion. After separation of the organic phase, the presence of the described compounds was evidenced by thin layer chromatography.

EXAMPLE 6

In this run, the procedure as set forth in Example 5 was repeated and all the reaction conditions were as described except that a lower alkanol, ethanol, was employed for the aromatic solvent benzene. The presence of the earlier described compounds was ascertained by thin layer chromotography.

EXAMPLE 7

The extraction procedure used herein employed water for the extraction of the ground cortex to form an emulsion which emulsion was centrifuged to remove solids. The emulsion was then extracted an immiscible organic solvent which yielded on separating the phases and drying of the organic layer and removing the organic solvent to give approximately the total organic extractibles.

EXAMPLE 8

A hexane extract prepared according to Example 1 was treated with 5% aqueous sodium bicarbonate, and, after separation of the phases, and acidification of the aqueous phase with a mineral acid the aqueous phase was back extracted with chloroform. The chloroform layer after separation, drying, and concentration yielded nearly pure 15-epi-PGA$_2$.

In the present invention the extraction of the gorgonian is generally advantageously performed by first extracting with solvents such as alkanols such as methanol, ethanol, isopropanol, n-butanol and the like; by aromatic solvents such as benzene, toluene, xylene and the like; by cycloalkyls such as, cyclohexane, cyclooctane, cyclohexene, cyclooctene, and the like; and by aliphatic solvents such as hexane, pentane, 2-methylpentene-1, 2-ethyl, 3-methyl-hexane, and the like. Exemplary of other solvents employed herein are, methylene chloride, chloroform, ethylene dichloride, methylchloroform, perchloromethylene and the like. Also suitable for the present purpose are ketones such as acetone, methyl isobutyl ketone and the like; esters such as ethylacetate, amyl acetate, methyl butyrate and the like; and ethers such as dimethyl ether, diethyl ether, methyl isobutyl ether, furan, tetrahydrofuran and the like.

The column support systems suitable for performing according to the mode and manner of the present invention include for example silica gel, neutral or acidic alumina, Florisil, silicic acid and the like. Other means for the purification of the novel compounds of the invention include reverse phase partition chromatography, countercurrent distribution, preparative paper chromatography, adsorption chromatography and combinations thereof.

The novel compounds of the invention are useful alone as anti-bacterial agents and as intermediates for making other biologically active prostaglandins. When the novel compounds are used as intermediates, for example, 15(R)-hydroxy-9-oxo-5-cis,10,13-trans-prostatrienoic acid can easily be converted by epimerization of the allylic alcohol by known techniques to produce 15(S)-hydroxy-9-oxo-5-cis,10,13-trans-prostatrienoic acid which has art known biologically acceptable activities, for example, blood pressure lowering, and smooth muscle activity. The compounds are useful singly, as antibacterial agents, and they demonstrate antibacterial activity against staphylococcus aureus. The compounds employed for this latter use can be combined with various non-toxic acceptable inert carriers in the form of powders, sprays, aqueous suspensions, ointments and the like. In general, the effective compounds can be formulated into pharmaceutical forms at concentration levels ranging from about 0.5% to about 50% by weight.

While the invention has been described with reference to certain preferred embodiments thereof, those skilled in the art will appreciate that various modifications, changes, omissions and substitutions can be made without departing from the spirit of the invention.

We claim:

1. A composition of matter consisting essentially of a compound of the formula

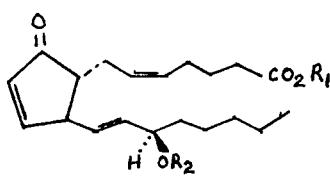

wherein $R_1$ is a member selected from the group consisting of H and $CH_3-$, and $R_2$ is a member selected from the group consisting of H and $CH_3CO-$.

2. A composition of matter according to claim 1 wherein the compound is 15(R)-hydroxy-9-oxo-5-cis, 10,13-trans-prostatrienoic acid.

3. A composition of matter according to claim 1 wherein the compound is methyl 15-(R)-acetoxy-9-oxo-5-cis, 10,13-trans-prostatrienoate.

4. A composition of matter according to claim 1 wherein the compound is methyl 15-(R)-hydroxy-9-oxo-5-cis, 10,13-trans-prostatrienoate.

5. A process for obtaining prostaglandin in usable form, which process comprises separating prostaglandin from the cortex of a gorgonian *Plexaura homomalla*, and recovering prostaglandin in usable form.

6. The process described in claim 5 wherein separating prostaglandin from the cortex of the gorgonian includes contacting the cortex with a solvent for the prostaglandin to form an extract containing the prostaglandin.

7. The process described in claim 6 wherein the cortex is separated from the inner skeleton of the gorgonian, and then ground to provide better contact with the solvent.

8. The process described in claim 6 wherein said solvent is an organic solvent.

9. The process described in claim 5 wherein the prostaglandin has the formula

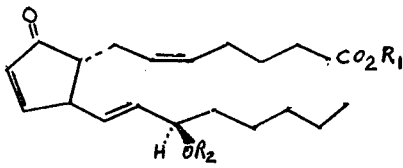

wherein $R_1$ is a member selected from the group consisting of H and $CH_3-$, and $R_2$ is a member selected from the group consisting of H and $CH_3CO-$.

10. The prostaglandin product of the process defined in claim 5.

11. The prostaglandin product of the process defined in claim 6.

12. A process for obtaining prostaglandin in usable form, which process comprises contacting the cortex of the gorgonian *Plexaura homomalla* with a material for extracting prostaglandin therefrom to form an extract containing prostaglandin, fractionating the extract to obtain a fraction containing prostaglandin, and recovering prostaglandin in usable form.

13. The process described in claim 12 wherein the cortex is ground to provide better contact with the material.

14. The process described in claim 12 wherein said fractionating includes chromatographic fractionating.

15. The process described in claim 12 wherein said material is an organic solvent for prostaglandin.

16. The process described in claim 12 wherein said material is an aqueous medium.

17. The process described in claim 12 wherein the prostaglandin has the formula

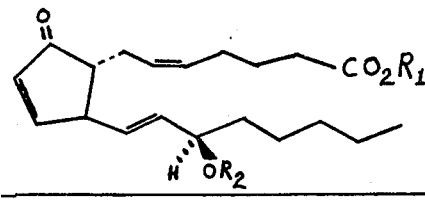

wherein $R_1$ is a member selected from the group consisting of H and $CH_3-$, and $R_2$ is a member selected from the group consisting of H and $CH_3CO-$.

18. The process described in claim 17 wherein the cortex is ground to provide better contact with the material, and said fractionating includes chromatographic fractionating.

19. The prostaglandin product of the process defined in claim 12.

* * * * *